(12) United States Patent
Wilson et al.

(10) Patent No.: US 11,891,510 B2
(45) Date of Patent: Feb. 6, 2024

(54) POLOXAMER COMPOSITIONS AND METHODS OF MAKING AND USING SAME

(71) Applicant: Sigma-Aldrich Co. LLC, St. Louis, MO (US)

(72) Inventors: Scott Wilson, Lenexa, KS (US); Kevin Kent, St. Louis, MO (US); Chandana Sharma, Lenexa, KS (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 0 days.

(21) Appl. No.: 16/645,915

(22) PCT Filed: Dec. 6, 2018

(86) PCT No.: PCT/US2018/064350
§ 371 (c)(1),
(2) Date: Mar. 10, 2020

(87) PCT Pub. No.: WO2019/125783
PCT Pub. Date: Jun. 27, 2019

(65) Prior Publication Data
US 2021/0347987 A1    Nov. 11, 2021

Related U.S. Application Data

(60) Provisional application No. 62/608,826, filed on Dec. 21, 2017.

(51) Int. Cl.
*C08L 71/02* (2006.01)
*C08L 71/00* (2006.01)
*C12N 5/00* (2006.01)

(52) U.S. Cl.
CPC .............. *C08L 71/02* (2013.01); *C08L 71/00* (2013.01); *C12N 5/0043* (2013.01)

(58) Field of Classification Search
CPC ........ C08L 71/02; C08L 71/00; C12N 5/0043
USPC ........................................................ 528/403
See application file for complete search history.

(56) References Cited

U.S. PATENT DOCUMENTS

| | | | |
|---|---|---|---|
| 3,579,465 A | 5/1971 | Schmolka | |
| 3,740,421 A | 6/1973 | Schmolka | |
| 5,523,492 A * | 6/1996 | Emanuele | A61P 7/02 568/624 |
| 2003/0206910 A1 | 11/2003 | Nicol et al. | |
| 2016/0002401 A1 * | 1/2016 | Emanuele | C08G 65/08 424/78.3 |
| 2016/0131634 A1 | 5/2016 | Hu et al. | |
| 2019/0085125 A1 | 3/2019 | Licht et al. | |

FOREIGN PATENT DOCUMENTS

| | | | |
|---|---|---|---|
| CN | 105582543 A | 5/2016 | |
| JP | 6-506258 A | 7/1994 | |

(Continued)

OTHER PUBLICATIONS

International Search Report and Written Opinion received for International Patent Application No. PCT/US2018/064350, dated Mar. 25, 2019, 08 pages.

(Continued)

*Primary Examiner* — David T Karst
(74) *Attorney, Agent, or Firm* — Benjamin J. Sodey; Sigma-Aldrich Co. LLC

(57) ABSTRACT

Described herein are poloxamer compositions for use as a shear protectant in cell culture and methods for preparing and using such compositions.

10 Claims, 4 Drawing Sheets

(56) References Cited

FOREIGN PATENT DOCUMENTS

| | | |
|---|---|---|
| JP | 9-506029 A | 6/1997 |
| JP | 2001-505058 A | 4/2001 |
| JP | 2017-516459 A | 6/2017 |
| JP | 2017-523282 A | 8/2017 |
| JP | 2019-511606 A | 4/2019 |
| KR | 10-2017-0029562 A | 3/2017 |
| WO | 92/16484 A1 | 10/1992 |
| WO | 95/08389 A1 | 3/1995 |
| WO | 2015/148736 A1 | 10/2015 |
| WO | WO-2015148736 A1 * | 10/2015 ............... C07K 1/02 |
| WO | 2016/007537 A1 | 1/2016 |
| WO | 2017/157505 A1 | 9/2017 |
| WO | 2019/125783 A1 | 6/2019 |

OTHER PUBLICATIONS

Office Action received for Chinese Patent Application No. 201880082440.2 dated Jul. 27, 2022, 18 Pages (11 Pages of English Translation & 7 Pages of Official Copy).

Office Action received for Korean Patent Application No. 10-2020-7020989, dated Sep. 29, 2022, 4 Pages (1 Pages of English translation & 3 Pages of official copy).

Communication pursuant to Article 94(3) EPC received for European Patent Application No. 18829617.2, dated Oct. 19, 2022, 4 Pages.

Office Action received for Chinese Patent Application No. 201880082440.2, dated Jan. 20, 2023, 17 Pages (10 Pages of English translation & 7 Pages of Official Copy).

Office Action received for Chinese Patent Application No. 201880082440.2 dated Jul. 29, 2023, 9 Pages. (6 Pages of English translation & 3 Pages of official copy).

International Preliminary Report on Patentability received for PCT Application No. PCT/US2018/064350, dated Oct. 17, 2020, 7 Pages.

Peng, H., "Development of small scale cell culture models for screening poloxamer 188 lot-to-lot variation", Biotechnology Progress, vol. 30, No. 6, Aug. 19, 2014, pp. 1411-1418.

Hagers Handbuch der Pharmazeutischen Praxis, vol. 9 "Stoffe P-Z", 1994, pp. 282 to 284.

* cited by examiner

POLOXAMER COMPOSITIONS AND METHODS OF MAKING AND USING SAME

RELATED APPLICATIONS

The present application is a US National Stacie application of International Application No. PCT/US2018/064350, filed Dec. 6, 2018, which claims the benefit of priority of U.S. Provisional Application No. 62/608,826, filed Dec. 21, 2017, the entirety content of each of which is incorporated herein by reference.

FIELD OF THE DISCLOSURE

The present disclosure generally relates to poloxamer compositions for use as a shear protectant in cell culture and methods for preparing and using such compositions.

BACKGROUND OF THE DISCLOSURE

Poloxamers, especially Poloxamer 188, are used in many industrial applications, cosmetics and pharmaceuticals. They are also used in cell culture media processes. The addition of poloxamers, especially Poloxamer 188, to cell culture media improves cell viability significantly. High cell viability is crucial for optimal protein production. Why poloxamers improve cell viability is not fully understood. It is believed that poloxamers reduce shear stress and in this way protect the cells from damage. Poloxamer, being a nonionic surfactant, is likely to concentrate at the gas bubble/medium interface and could prevent cell attachment to gas bubbles and in this way prevent cells from damage when gas bubbles burst. It may also reduce shock when bubbles burst. Some publications claim that poloxamers improve the oxygen transfer rate from the gas into the liquid phase, but other publications contradict these findings. There are also indications that poloxamers may "repair" small defects in cell membranes.

In general, a poloxamer is a polyethylene glycol (PEG)/polypropylene glycol (PPG) tri-block copolymer, CAS number 9003-11-6, having the general formula I:

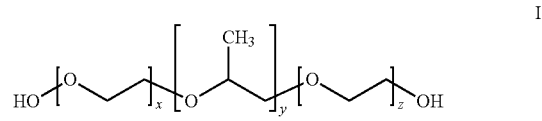

with x and z preferably independently being 5 to 150 and y preferably being 15 to 67.

Conventionally-used product known as Poloxamer 188 has an average molecular weight between 7680 and 9510 g/mol (defined and determined according to pharmacopeia). In formula I, for Poloxamer 188 x and z are each around 80 and y is around 27. This compound is commercially available as Poloxamer 188, Pluronic® F 68, Kolliphor® P 188, Lutrol® F 68, SYNPERONIC™ PE/F 68 or PLONON #188P. They are commercially available in a variety of physical forms (Pluronics® or Lutrole®, e.g., a Pluronic® solution, gel, or solid, such as Pluronic® F-68). Alternatively, poloxamers can be made from raw materials according to methods known in the art (see, for example, U.S. Pat. Nos. 3,579,465 and 3,740,421). Further information about poloxamers can be found in Hagers Handbuch der Pharmazeutischen Praxis, volume 9 "Stoffe P-Z", 1994, pages 282 to 284.

Significant lot-to-lot variability is observed in commercially available poloxamers like Poloxamer 188 lots when used in cell culture media. As a consequence some lots are not suitable for the use in cell culture, because they do not protect cells sufficiently from damage/death. The reason for this is still not fully understood. As a consequence cell viability is significantly lower when these "bad" lots are used.

SUMMARY OF THE DISCLOSURE

Among the various aspects of the present disclosure is the provision of a poloxmer composition having a lower average molecular weight as compared to Poloxamer 188. Methods of making the poloxamer compositions and uses of the same are also provided.

Briefly, therefore, the present disclosure is directed to a poloxamer composition having the formula I:

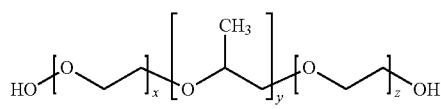

wherein y is about 15 to about 26; the sum of x and z is from about 81 to about 100; and the composition has an average molecular weight in the range of about 6,000 g/mol to about 8,000 g/mol.

Another aspect of the disclosure is directed to method of making the poloxamer composition substantially as disclosed herein and in the accompanying Figures. Still another aspect of the disclosure is directed to the use of the poloxamer composition substantially as disclosed herein and in the accompanying Figures. Other aspects of the disclosure are directed to the methods, compositions, uses, and inventions as substantially disclosed herein and in the accompanying Figures.

Other objects and features will be in part apparent and in part pointed out hereinafter.

DETAILED DESCRIPTION

Figure 1:
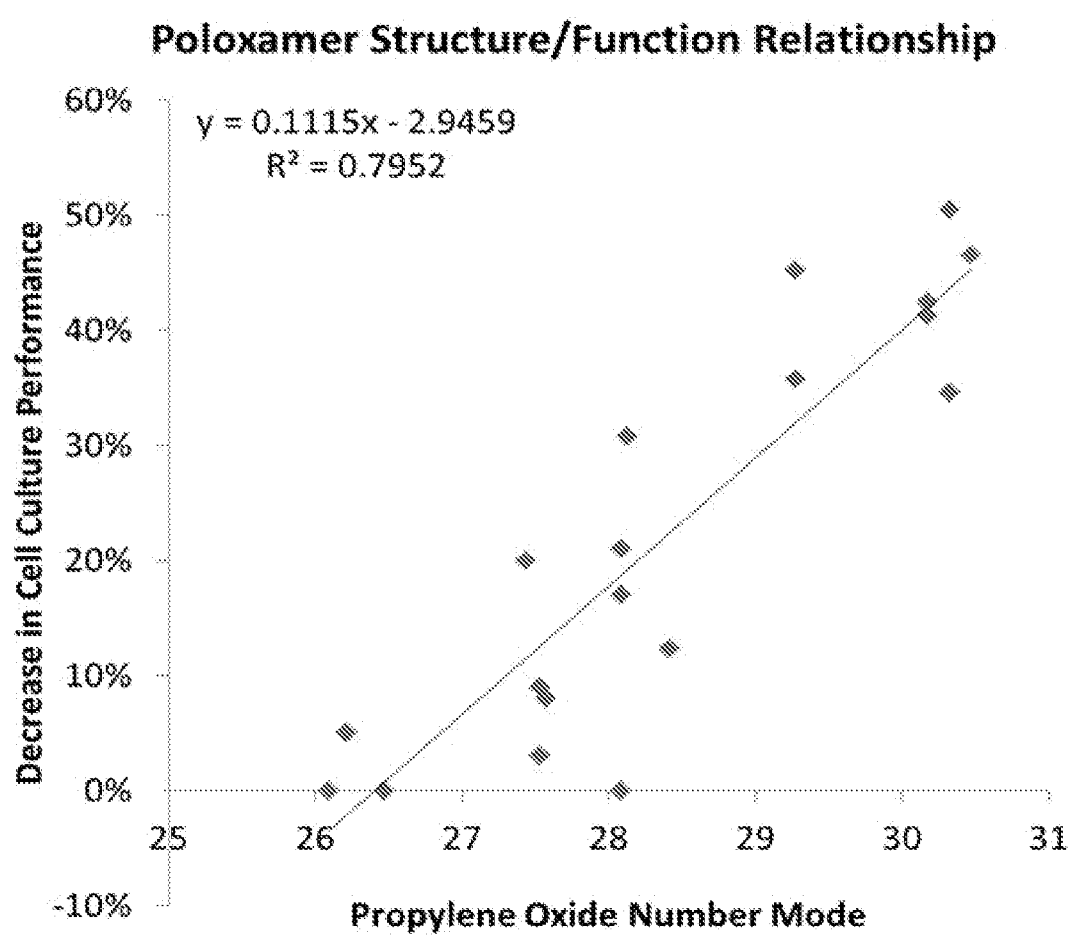
FIG. 1 is a plot of the cell culture performance of 19 lots of Poloxamer 188 against the mode of the propylene oxide distribution in each lot of Poloxamer 188. The cell culture performance was measured by a biological assay as described in the Examples, and the propylene oxide distribution was measured by an analytical reverse phase UPLC/MS method described in the Examples. The USP Specification allows for 21.6 to 33 average propylene oxide units in Poloxamer 188 (assuming no interfering species).

One aspect of the present disclosure is directed to a poloxamer composition.

A person skilled in the art knows how to use poloxamers as ingredients in cell culture media. They are aware of the suitable amount and format to use. But sometimes, cell culture, even if it was prepared according to standard procedures and recipe, does not perform as good as it typically does. It has been found that this might be due to the poloxamer. In such a case, until now the whole lot of poloxamer had to be discarded.

The identification of a lot of poloxamer that does not perform as well as expected can be, e.g., done in cell culture. If a cell culture comprising poloxamer does not show a cell viability and performance as expected one might try to improve this by providing a low average molecular weight poloxamer according to the present disclosure.

Any cell culture that does not perform as expected can trigger a substitution of conventional poloxamer for the poloxamer according to the present disclosure. It is also possible to do cell culture tests in advance of the actual cell culture. An experimental set-up to investigate the performance of the cell culture could be as follows:

A suitable experimental set-up is the small scale baffled shake flask model described in Haofan Peng et al., Biotechnol. Prog., 2014, Vol. 30 (6), 1411-1418.

The skilled person is well aware that:
- different concentrations of poloxamer can be used (typically between 0.1 and 5 g/L).
- any type of CHO cells or other cells can be used
- any type of cell culture medium suitable for the chosen cell line can be used.
- cultivation takes preferably place on an orbital shaker and speed and throw may need to be adjusted to the chosen cell line and cultivation conditions.
- depending on chosen parameters described above, viability drop may be measured at a suitable time point between 2 hours and 5 days.

The definition of cell viability according to the present invention is the percentage of living cells in a solution as determined by, e.g., a Trypan blue assay in a Beckman-Coulter ViCell XR or similar.

As we have surprisingly discovered that low average molecular weight poloxamer provides superior performance, it is also possible to analyze each lot of poloxamer prior to its use and/or manufacture the low average molecular weight poloxamer according to specification. The analysis can, e.g., be performed by SEC (size exclusion chromatography).

Poloxamer Compositions

In general, the poloxamer compositions of the present disclosure have a lower average molecular weight than conventional poloxamer materials, e.g., Poloxamer 188, and this composition provides surprisingly superior results when used, for instance, in cell culture as described herein. A particular poloxamer composition in accordance with the present disclosure has the formula I:

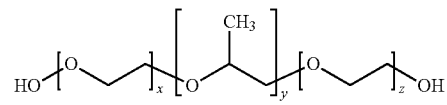

wherein y is about 15 to about 26; the sum of x and z is from about 81 to about 100; and the composition has an average molecular weight in the range of about 6,000 g/mol to about 8,000 g/mol.

As noted above in connection with formula I, y is about 15 to about 26. In some embodiments in connection with formula I, for example, y is about 15, about 16, about 17, about 18, about 19, about 20, about 21, about 22, about 23, about 24, about 25, or about 26.

In other embodiments in connection with formula I, for example, y is about 15 to about 25, about 15 to about 24, about 15 to about 23, about 15 to about 22, about 15 to about 21, about 15 to about 20, about 15 to about 19, about 15 to about 18, about 15 to about 17, or about 15 to about 16. In other embodiments in connection with formula I, for example, y is about 16 to about 25, about 16 to about 24, about 16 to about 23, about 16 to about 22, about 16 to about 21, about 16 to about 20, about 16 to about 19, about 16 to about 18, or about 16 to about 17. In other embodiments in connection with formula I, for example, y is about 17 to about 25, about 17 to about 24, about 17 to about 23, about 17 to about 22, about 17 to about 21, about 17 to about 20, about 17 to about 19, or about 17 to about 18. In other embodiments in connection with formula I, for example, y is about 18 to about 25, about 18 to about 24, about 18 to about 23, about 18 to about 22, about 18 to about 21, about 18 to about 20, or about 18 to about 19. In other embodiments in connection with formula I, for example, y is about 19 to about 25, about 19 to about 24, about 19 to about 23, about 19 to about 22, about 19 to about 21, or about 19 to about 20. In other embodiments in connection with formula I, for example, y is about 20 to about 25, about 20 to about 24, about 20 to about 23, about 20 to about 22, or about 20 to about 21. In other embodiments in connection with formula I, for example, y is about 21 to about 25, about 21 to about 24, about 21 to about 23, or about 21 to about 22. In other embodiments in connection with formula I, for example, y is about 22 to about 25, about 22 to about 24, or about 22 to about 23. In other embodiments in connection with formula I, for example, y is about 23 to about 25, or about 23 to about 24. In other embodiments in connection with formula I, for example, y is about 24 to about 25.

As noted above in connection with formula I, the sum of x and z is about 81 to about 100. In some embodiments in connection with formula I, for example, the sum of x and z is about 81, about 82, about 83, about 84, about 85, about 86, about 87, about 88, about 89, about 90, about 91, about 92, about 93, about 94, about 95, about 96, about 97, about 98, about 99, or about 100.

In other embodiments in connection with formula I, for example, the sum of x and z is about 81 to about 99, about 81 to about 98, about 81 to about 97, about 81 to about 96, about 81 to about 95, about 81 to about 94, about 81 to about 93, about 81 to about 92, about 81 to about 91, about 81 to about 90, about 81 to about 89, about 81 to about 88, about 81 to about 87, about 81 to about 86, about 81 to about 85, about 81 to about 84, about 81 to about 83, or about 81 to about 82. In other embodiments in connection with formula I, for example, the sum of x and z is about 82 to about 99, about 82 to about 98, about 82 to about 97, about 82 to about 96, about 82 to about 95, about 82 to about 94, about 82 to about 93, about 82 to about 92, about 82 to about 91, about 82 to about 90, about 82 to about 89, about 82 to about 88, about 82 to about 87, about 82 to about 86, about 82 to about 85, about 82 to about 84, or about 82 to about 83. In other embodiments in connection with formula I, for example, the sum of x and z is about 83 to about 99, about 83 to about 98, about 83 to about 97, about 83 to about 96, about 83 to about 95, about 83 to about 94, about 83 to about 93, about 83 to about 92, about 83 to about 91, about 83 to about 90, about 83 to about 89, about 83 to about 88, about 83 to about 87, about 83 to about 86, about 83 to about 85, or about 83 to about 84. In other embodiments in connection with formula I, for example, the sum of x and z is about 84 to about 99, about 84 to about 98, about 84 to about 97, about 84 to about 96, about 84 to about 95, about 84 to about 94, about 84 to about 93, about 84 to about 92, about 84 to about 91, about 84 to about 90, about 84 to about 89, about 84 to about 88, about 84 to about 87, about 84 to about 86, or about 84 to about 85. In other embodiments in connection with formula I, for example, the sum of x and z is about 85 to about 99, about 85 to about 98, about 85 to about 97, about 85 to about 96, about 85 to about 95, about 85 to about 94, about 85 to about 93, about 85 to about 92, about 85 to about 91, about 85 to about 90, about 85 to about 89, about 85 to about 88, about 85 to about 87, or about 85 to about 86. In other embodiments in connection with formula I, for example, the sum of x and z is about 86 to about 99, about 86 to about 98, about 86 to about 97, about 86 to about 96, about 86 to about 95, about 86 to about 94, about 86 to about 93, about 86 to about 92, about 86 to about 91, about 86 to about 90, about 86 to about 89, about 86 to about 88, or about 86 to about 87. In other embodiments in connection with formula I, for example, the sum of x and z is about 87 to about 99, about 87 to about 98, about 87 to about 97, about 87 to about 96, about 87 to about 95, about 87 to about 94, about 87 to about 93, about 87 to about 92, about 87 to about 91, about 87 to about 90, about 87 to about 89, or about 87 to about 88. In other embodiments in connection with formula I, for example, the sum of x and z is about 88 to about 99, about 88 to about 98, about 88 to about 97, about 88 to about 96, about 88 to about 95, about 88 to about 94, about 88 to about 93, about 88 to about 92, about 88 to about 91, about 88 to about 90, or about 88 to about 89. In other embodiments in connection with formula I, for example, the sum of x and z is about 89 to about 99, about 89 to about 98, about 89 to about 97, about 89 to about 96, about 89 to about 95, about 89 to about 94, about 89 to about 93, about 89 to about 92, about 89 to about 91, or about 89 to about 90. In other embodiments in connection with formula I, for example, the sum of x and z is about 90 to about 99, about 90 to about 98, about 90 to about 97, about 90 to about 96, about 90 to about 95, about 90 to about 94, about 90 to about 93, about 90 to about 92, or about 90 to about 91. In other embodiments in connection with formula I, for example, the sum of x and z is about 91 to about 99, about 91 to about 98, about 91 to about 97, about 91 to about 96, about 91 to about 95, about 91 to about 94, about 91 to about 93, or about 91 to about 92. In other embodiments in connection with formula I, for example, the sum of x and z is about 92 to about 99, about 92 to about 98, about 92 to about 97, about 92 to about 96, about 92 to about 95, about 92 to about 94, or about 92 to about 93. In other embodiments in connection with formula I, for example, the sum of x and z is about 93 to about 99, about 93 to about 98, about 93 to about 97, about 93 to about 96, about 93 to about 95, or about 93 to about 94. In other embodiments in connection with formula I, for example, the sum of x and z is about 94 to about 99, about 94 to about 98, about 94 to about 97, about 94 to about 96, or about 94 to about 95. In other embodiments in connection with formula I, for example, the sum of x and z is about 95 to about 99, about 95 to about 98, about 95 to about 97, or about 95 to about 96. In other embodiments in connection with formula I, for example, the sum of x and z is about 96 to about 99, about 96 to about 98, or about 96 to about 97. In other embodiments in connection with formula I, for example, the sum of x and z is about 97 to about 99, or about 97 to about 98. In other embodiments in connection with formula I, for example, the sum of x and z is about 98 to about 99.

As noted above in connection with formula I, the composition has an average molecular weight in the range of about 6,000 to about 8,000 g/mol. In some embodiments in connection with formula I, for example, the composition has an average molecular weight of about 6,000 g/mol, about 6,200 g/mol, about 6,400 g/mol, about 6,600 g/mol, about 6,800 g/mol, about 7,000 g/mol, about 7,200 g/mol, about 7,400 g/mol, about 7,600 g/mol, about 7,800 g/mol, or about 8,000 g/mol.

In other embodiments in connection with formula I, for example, the composition has an average molecular weight in the range of about 6,000 g/mol to about 7,600 g/mol, about 6,000 g/mol to about 7,400 g/mol, about 6,000 g/mol to about 7,200 g/mol, about 6,000 g/mol to about 7,000 g/mol, about 6,000 g/mol to about 6,800 g/mol, about 6,000 g/mol to about 6,600 g/mol, about 6,000 g/mol to about 6,400 g/mol, or about 6,000 g/mol to about 6,200 g/mol. In other embodiments in connection with formula I, for example, the composition has an average molecular weight in the range of about 6,200 g/mol to about 7,600 g/mol, about 6,200 g/mol to about 7,400 g/mol, about 6,200 g/mol to about 7,200 g/mol, about 6,200 g/mol to about 7,000 g/mol, about 6,200 g/mol to about 6,800 g/mol, about 6,200 g/mol to about 6,600 g/mol, or about 6,200 g/mol to about 6,400 g/mol. In other embodiments in connection with formula I, for example, the composition has an average molecular weight in the range of about 6,400 g/mol to about 7,600 g/mol, about 6,400 g/mol to about 7,400 g/mol, about 6,400 g/mol to about 7,200 g/mol, about 6,400 g/mol to about 7,400 g/mol, about 6,400 g/mol to about 6,800 g/mol, or about 6,400 g/mol to about 6,600 g/mol. In other embodiments in connection with formula I, for example, the composition has an average molecular weight in the range of about 6,600 g/mol to about 7,600 g/mol, about 6,600 g/mol to about 7,400 g/mol, about 6,600 g/mol to about 7,200 g/mol, about 6,600 g/mol to about 7,000 g/mol, or about 6,600 g/mol to about 6,800 g/mol. In other embodiments in connection with formula I, for example, the composition has an average molecular weight in the range of about 6,800 g/mol to about 7,600 g/mol, about 6,800 g/mol to about 7,400 g/mol, about 6,800 g/mol to about 7,200 g/mol, or about 6,800 g/mol to about 7,000 g/mol. In other embodiments in connection with formula I, for example, the composition has an average molecular weight in the range of about 7,000 g/mol to about 7,600 g/mol, about 7,000 g/mol to about 7,400 g/mol, or about 7,000 g/mol to about 7,200 g/mol. In other embodiments in connection with formula I, for example, the composition has an average molecular weight in the range of about 7,200 g/mol to about 7,600 g/mol, or about 7,200 g/mol to about 7,400 g/mol.

In combination, in some embodiments in connection with formula I, for example, y is about 15, about 16, about 17, about 18, about 19, about 20, about 21, about 22, about 23, about 24, about 25, or about 26; the sum of x and z is about 81, about 82, about 83, about 84, about 85, about 86, about 87, about 88, about 89, about 90, about 91, about 92, about 93, about 94, about 95, about 96, about 97, about 98, about 99, or about 100; and an average molecular weight of about 6,000 g/mol, about 6,200 g/mol, about 6,400 g/mol, about 6,600 g/mol, about 6,800 g/mol, about 7,000 g/mol, about 7,200 g/mol, about 7,400 g/mol, or about 7,600 g/mol.

Methods of Preparing Poloxamer Compositions

In general, any conventional methods for making poloxamers can be used to make the poloxamer compositions disclosed herein (e.g., the composition having the formula I, above). Typically, using conventional processes, shorter reaction times and/or temperatures may be used to create the lower molecular weight poloxamer compositions having the formula I, above.

Additionally or alternatively, it may be desirable in some embodiments to purify the poloxamer compositions in accordance with the method disclosed in International Application No. PCT/EP2017/000238 (hereby incorporated by reference herein).

Use of Poloxamer Compositions in Cell Culture

The poloxamer composition described herein can be used in cell culture. If its particle size needs to be adjusted, it can optionally be milled prior to adding it to the cell culture medium.

A cell culture is any setup in which cells are cultured.

A cell culture can be performed in any container suitable for the culture of cells, such as a petri dish, contact plate, bottle, tube, well, vessel, bag, flask and/or tank. Preferably, it is performed in a bioreactor. Typically the container is sterilized prior to use. Culturing is typically performed by incubation of the cells in an aqueous cell culture medium under suitable conditions such as suitable temperature, osmolality, aeration, agitation, etc. which limit contamination with foreign microorganisms from the environment. A person skilled in the art is aware of suitable incubation conditions for supporting or maintaining the growth/culturing of cells.

A cell culture medium (synonymously used: culture medium) according to the present invention is any mixture of components which maintains and/or supports the in vitro growth of cells and/or supports a particular physiological state. It is also suitable for pre-enrichment cultures as well as for use as a maintenance medium.

Preferably, it is a chemically defined medium. The cell culture medium can comprise all components necessary to maintain and/or support the in vitro growth of cells or be used for the addition of selected components in combination with or not in combination with further components that are added separately (media supplement). Preferably, the cell culture medium comprises all components necessary to maintain and/or support the in vitro growth of cells.

A cell culture medium which comprises all components necessary to maintain and/or support the in vitro growth of cells typically comprises at least one or more saccharide components, one or more amino acids, one or more vitamins or vitamin precursors, one or more salts, one or more buffer components, one or more co-factors and one or more nucleic acid components (nitrogenous bases) or their derivatives. It may also comprise chemically defined biochemicals such as recombinant proteins, e.g., rInsulin, rBSA, rTransferrin, rCytokines etc.

Cell culture media can be in the form of aqueous liquids or in the form of dry powders which for use are dissolved in water or an aqueous buffer.

A person skilled in the art is able to choose a suitable cell culture medium for the specific envisaged purpose.

Abbreviations and Definitions

The following definitions and methods are provided to better define the present invention and to guide those of ordinary skill in the art in the practice of the present invention. Unless otherwise noted, terms are to be understood according to conventional usage by those of ordinary skill in the relevant art.

It must be noted that, as used in this specification and the appended claims, the singular form "a," "an" and "the" include plural referents unless the context clearly dictates otherwise. Thus, for example, reference to "a poloxamer" includes a plurality of poloxamers, and the like.

Unless defined otherwise, all technical and scientific terms used herein have the same meaning as commonly understood by one of ordinary skill in the art to which this invention is related. The following terms are defined for purposes of the invention as described herein.

The term "bioreactor," as used herein, refers to any manufactured or engineered device or system that supports a biologically active environment. In some instances, a bioreactor is a vessel in which a cell culture process is carried out which involves organisms or biochemically active substances derived from such organisms. Such a process may be either aerobic or anaerobic. Commonly used bioreactors are typically cylindrical, ranging in size from liters to cubic meters, and are often made of stainless steel. In some embodiments described herein, a bioreactor might contain a disposable constituent made of a material other than steel and is disposable. In some embodiments that is a disposable bag where in the biologically active environment is maintained. It is contemplated that the total volume of a bioreactor may be any volume ranging from 100 mL to up to 10,000 Liters or more, depending on a particular process.

Average molecular weight according to pharmacopeia is determined by titration using a phthalic anhydride-pyridine solution.

Average molecular weight determined by SEC is determined as follows:

weight average molecular weight: $M_w = \Sigma_i N_i M_i^2/(\Sigma_i N_i M_i)$ number average molecular weight: $M_n = \Sigma_i N_i M_i/(\Sigma_i N_i)$ peak molecular weight: $M_p$=molecular weight at maximum $N_i$ $N_i$=number of polymer species in fraction i $M_i$=molecular weight of polymer species in fraction i SEC conditions:

Calibration standards: PEG (details see example 7)

Eluent: THF

Flow rate: 1 ml/min

Injection volume: 100 μl

Column: particle size=5 μm, material=styrene-divinylbenzene

Temperature: 40° C.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

In order to investigate deficiencies in Poloxamer 188 performance a biological cell culture assay was developed that puts mammalian cells under high shear stress. An analytical method for elucidating the structure of Poloxamer 188 was developed which is capable of distinguishing relative distributions of propylene oxide (one of the two monomeric units in the polymer) in Poloxamer 188. During the course of the investigation a negative correlation between PO content and performance in the biological functional assay was observed. All samples evaluated were within USP specification for Poloxamer 188, but variability within the specification has an effect on performance (see FIG. 1). The negative correlation between propylene oxide distribution mode and biological function suggests that there may be an optimum poloxamer chemical structure for cell culture at lower PO content. Lots of Poloxamer 188 with % differences of 10% and above has been shown to affect customer performance of SAFC media. The analytical and biological methods are described below.

Example 2

Figure 2:
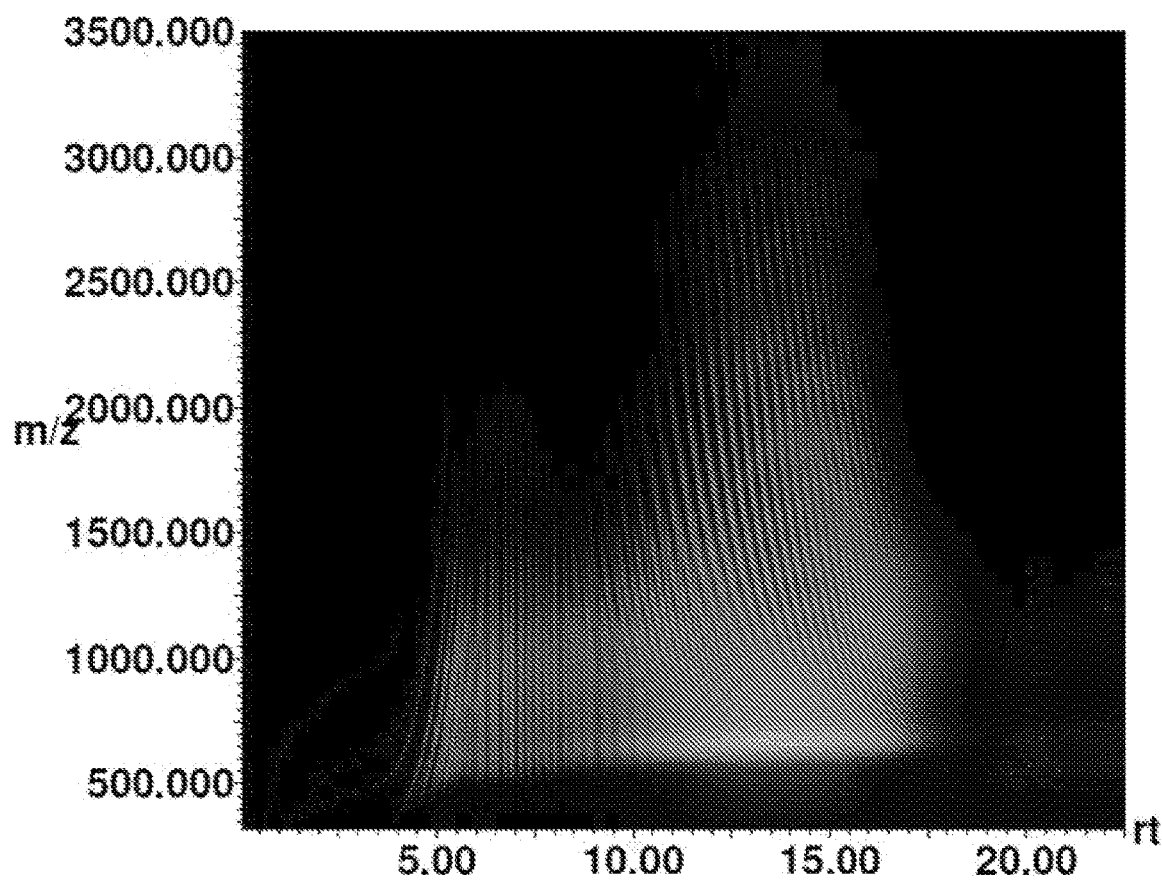
FIG. 2 is a 3D plot of the UPLC/MS chromatogram of a single lot of Poloxamer 188. The x-axis is the retention time of polymer, and the y-axis is the mass to charge ratio detected by the mass spectrometer. The intensity of each peak is shown by intensity of the red color. This is reverse phase chromatography, so polymers with retention times farther to the right are more hydrophobic, and for this particular polymer that means they have increasing chain lengths of PPO.

The analytical method is a reversed phase Ultra Performance Liquid Chromatography-Mass Spectrometry (UPLC/MS) method that separates the polymer largely according to the PPO chain length. A representative chromatogram from the method is shown in FIG. 2. Each of the vertical lines in the chromatogram is representative of an additional unit of propylene oxide, and lines that are not vertical are indicative of ethylene oxide having a small effect on the separation. Using the data shown in FIG. 2 the peak of the PPO chain length distribution can be identified, and was used to generate the data used in FIG. 1.

Example 3

Figure 3:
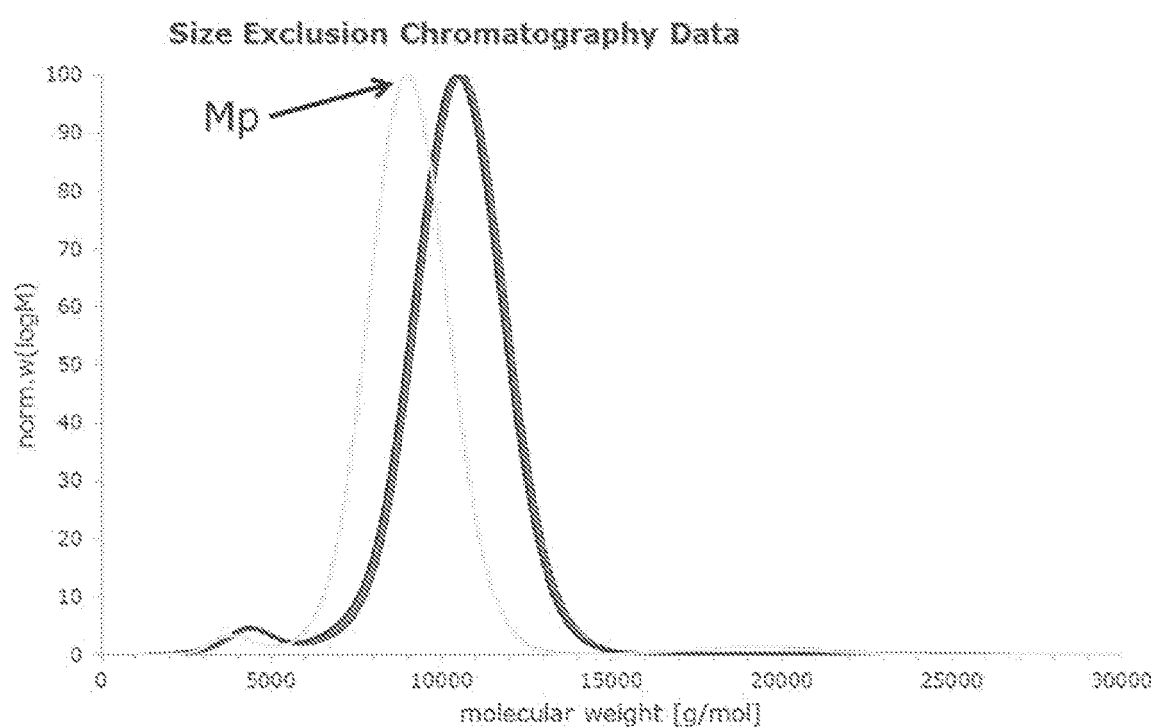
FIG. 3 is an SEC chromatogram comparing the molecular weight distribution of several Poloxamer 188 lots. Correlations to functionality are based upon peak molecular weight (Mp).

Additional data analyzing Poloxamer 188 using size exclusion chromatography has identified correlations to the polymers molecular weight and function. Poloxamer samples are evaluated using Polymer Standards Service (PSS) styrene-divinylbenzene (SDV) columns and PSS PEG calibration standards (Mp: 430-44000 g/mol) to determine the molecular weight. FIG. 3 is a SEC chromatogram that represents the molecular weight differences among Poloxamer 188 samples. As the main peaks shift to the left, the result is a smaller size peak molecular weight poloxamer (Mp). The current specification for Poloxamer 188 molecular weight is reported as an average. This data would include all peaks shown below, not the peak Poloxamer 188 molecular weight.

Example 4

Figure 4:
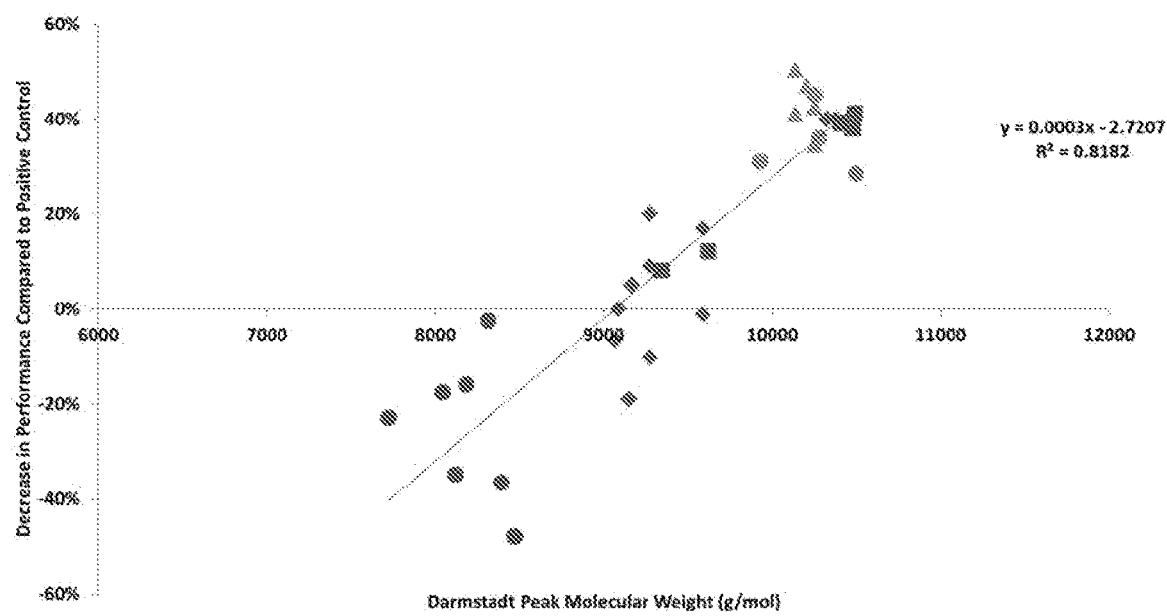
FIG. 4 is a plot of the relationship between the peak molecular weight (SEC) and the decrease in biological performance of Poloxamer 188. In this chart better performance is further negative, so it predicts that lower molecular weight Poloxamer 188 will have better performance in cell culture media.

A strong correlation between peak molecular weight of Poloxamer 188, and the performance of Poloxamer 188 was been observed. The relationship is observed in samples from 5 different suppliers comparing the performance calculated as a percent difference from a known control lot with 0% being equivalent to the control and negative percent improved from the control. The correlation coefficient measured for the relationship is 0.82. The chart in FIG. 4 predicts that lower peak molecular weights will have better performance.

What is claimed is:

1. A culture medium for in vitro culture of cells, the medium comprising a poloxamer composition derived from poloxamer 188 and having the formula I:

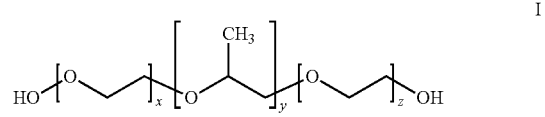

wherein x, y, and z are positive integers such that the composition has an average molecular weight in the range of about 6,000 g/mol to about 7,600 g/mol.

2. The culture medium of claim 1, wherein the composition has an average molecular weight in the range of about 6,000 g/mol to about 7,400 g/mol, about 6,000 g/mol to about 7,200 g/mol, about 6,000 g/mol to about 7,000 g/mol, about 6,000 g/mol to about 6,800 g/mol, about 6,000 g/mol to about 6,600 g/mol, about 6,000 g/mol to about 6,400 g/mol, or about 6,000 g/mol to about 6,200 g/mol.

3. The culture medium of claim 1, wherein the culture medium is a chemically defined medium.

4. The culture medium of claim 1, further comprising one or more saccharide components, one or more amino acids, one or more vitamins or vitamin precursors, one or more salts, one or more buffer components, or one or more co-factors.

5. A culture medium for in vitro culture of cells, the medium comprising a poloxamer composition derived from poloxamer 188, the composition having an average molecular weight in the range of about 6,000 g/mol to about 7,600 g/mol.

6. The culture medium of claim 5, wherein the composition has an average molecular weight in the range of about 6,000 g/mol to about 7,400 g/mol, about 6,000 g/mol to about 7,200 g/mol, about 6,000 g/mol to about 7,000 g/mol, about 6,000 g/mol to about 6,800 g/mol, about 6,000 g/mol to about 6,600 g/mol, about 6,000 g/mol to about 6,400 g/mol, or about 6,000 g/mol to about 6,200 g/mol.

7. The culture medium of claim 5, wherein the culture medium is a chemically defined medium.

8. The culture medium of claim 5, further comprising one or more saccharide components, one or more amino acids, one or more vitamins or vitamin precursors, one or more salts, one or more buffer components, or one or more co-factors.

9. The culture medium of claim 5, wherein the composition has an average molecular weight in the range of about 6,000 g/mol to about 7,000 g/mol, about 6,000 g/mol to about 6,800 g/mol, about 6,000 g/mol to about 6,600 g/mol, about 6,000 g/mol to about 6,400 g/mol, or about 6,000 g/mol to about 6,200 g/mol.

10. The culture medium of claim 5, wherein the composition has an average molecular weight in the range of about 6,000 g/mol to about 6,800 g/mol, about 6,000 g/mol to about 6,600 g/mol, about 6,000 g/mol to about 6,400 g/mol, or about 6,000 g/mol to about 6,200 g/mol.

* * * * *